United States Patent
Yi et al.

(10) Patent No.: US 10,017,537 B2
(45) Date of Patent: Jul. 10, 2018

(54) PEPTIDE SELECTIVELY BINDING TO GRAPHITIC MATERIALS AND VOLATILE ORGANIC COMPOUNDS

(71) Applicant: KOREA INSTITUTE OF SCIENCE AND TECHNOLOGY, Seoul (KR)

(72) Inventors: Hyunjung Yi, Seoul (KR); Ki Young Lee, Seoul (KR); Chaun Jang, Busan (KR); Joonyeon Chang, Seoul (KR); Sang Kyung Kim, Seoul (KR); Soomi Ju, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 176 days.

(21) Appl. No.: 14/793,032

(22) Filed: Jul. 7, 2015

(65) Prior Publication Data

US 2016/0031938 A1  Feb. 4, 2016

Related U.S. Application Data

(63) Continuation-in-part of application No. 14/171,898, filed on Feb. 4, 2014, now abandoned.

(30) Foreign Application Priority Data

| | | |
|---|---|---|
| Apr. 15, 2013 | (KR) | 10-2013-0041173 |
| Oct. 8, 2014 | (KR) | 10-2014-0135860 |
| Mar. 11, 2015 | (KR) | 10-2015-0034035 |

(51) Int. Cl.
 *C07K 7/06* (2006.01)
(52) U.S. Cl.
 CPC ..................... *C07K 7/06* (2013.01)
(58) Field of Classification Search
 CPC ........................................................ C07K 7/06
 See application file for complete search history.

(56) References Cited

U.S. PATENT DOCUMENTS

| | | | |
|---|---|---|---|
| 8,470,611 B2 | 6/2013 | Dang et al. | |
| 9,568,456 B2* | 2/2017 | Yi | G01N 33/0004 |
| 2005/0277160 A1 | 12/2005 | Shiba et al. | |
| 2006/0240534 A1* | 10/2006 | Yamaguchi | C12N 9/0006 435/131 |
| 2007/0117147 A1 | 5/2007 | Jagota et al. | |
| 2013/0230464 A1 | 9/2013 | Yi et al. | |
| 2014/0309126 A1 | 10/2014 | Yi et al. | |

FOREIGN PATENT DOCUMENTS

| | | |
|---|---|---|
| KR | 20100079579 A | 7/2010 |
| KR | 101188172 B1 | 9/2012 |
| KR | 101325282 B1 | 10/2013 |
| KR | 20140124067 A | 10/2014 |

OTHER PUBLICATIONS

Dunbar et al, Detection of Volatile Organic Compounds Using Porphyrin Derivatives, J. Phys. Chem. B, 2010, 114, pp. 11697-11702.*
Normand et al, Genome characteristics of facultatively symbiotic *Frankia* sp. strains reflect host range and host plant biogeography, Genome Res., 2007, 17, pp. 7-15.*
Peptidase M50-Frankia casuarinae, from https://www.ncbi.nlm.nih.gov/protein/ABD12926.1, pp. 1-2, accessed Jul. 10, 2017.*
Yampolsky et al, The Exchangeability of Amino Acids in Proteins, Genetics, 2005, 170, pp. 1459-1472.*
Tomasio et al, Modeling the Binding Affinity of Peptides for Graphitic Surfaces. Influences of Aromatic Content and Interfacial Shape, J. Phys. Chem. C, 2009, 113, pp. 8778-8785.*
Katoch et al, Structure of a Peptide Adsorbed on Graphene and Graphite, Nano Lett., 2012, 12, pp. 2342-2346.*
Khatayevich et al, Controlling the Surface Chemistry of Graphite by Engineered Self-Assembled Peptides, Langmuir, 2012, 28, pp. 8589-8593.*
Imai et al, Effect of protein properties on display efficiency using the M13 phage display system, Pharmazie, 2008, 63, pp. 760-764.*
Iannolo et al, Modifying Filamentous Phage Capsid: Limits in the Size of the Major Capsid Protein, J. Mol. Biol., 1995, 248, pp. 835-844.*
Segers et al, Evidence that RNA silencing functions as an antiviral defense mechanism in fungi, PNAS, 2007, 104, pp. 12902-12906.*
Dicer-like protein 1-Cryphonectria parasitica, from https://www.ncbi.nlm.nih.gov/protein/ABB00356.1, pp. 1-3, accessed Oct. 31, 2017.*
Sachdev S. Sidhu, et al; "High Copy Display of Large Proteins on Phage for Functional Selections", Journal of Molecular Biology, vol. 296, pp. 487-495; Feb. 19, 2000.
Bong Gill Choi, et al; "Solution Chemistry of Self-Assembled Graphene Nanohybrids for High-Performance Flexible Biosensors", ACSNano, vol. 4, No. 5, pp. 2910-2918; Published online Apr. 8, 2010.
Xiangnan Dang, et al; "Virus-templated self-assembled single-walled carbon nanotubes for highly efficient electron collection in photovoltaic devices", Nature Nanotechnology, vol. 6, pp. 377-384; Published online Apr. 24, 2011.
Wenzhao Jia, et al; "Electrochemical Tattoo Biosensors for Real-Time Noninvasive Lactate Monitoring in Human Perspiration", Anal. Chem. vol. 85, Jul. 1, 2013, pp. 6553-6560.
Yun Jung Lee, et al; "Fabricating Genetically Engineered High-Power Lithium-Ion Batteries Using Multiple Virus Genes", Science, vol. 324, May 22, 2009, pp. 1051-1055.
Seung-Wuk Lee, et al; "Chiral Smectic C Structures of Virus-Based Films", Langmuir, vol. 19, pp. 1592-1598, Published on Web Dec. 24, 2002.
Karen A Noren, et al; "Construction of High-Complexity Combinatorial Phage Display Peptide Libraries"; Methods, vol. 23, No. 2, pp. 169-178, Feb. 2001.

(Continued)

*Primary Examiner* — Julie Ha
*Assistant Examiner* — Li N Komatsu
(74) *Attorney, Agent, or Firm* — Ladas & Parry LLP; Loren K. Thompson

(57) ABSTRACT

Provided is a peptide including $X_2SX_1AAX_2X_3P$ (SEQ ID NO. 1), $X_2X_2PX_3X_2AX_3P$ (SEQ ID NO. 2), $SX_1AAX_2X_3P$ (SEQ ID NO. 3), or $X_2PX_3X_2AX_3P$ (SEQ ID NO. 4), which bind to graphitic materials or volatile organic compounds.

12 Claims, 14 Drawing Sheets

(56) References Cited

OTHER PUBLICATIONS

Cheol-Hwan Park, et al; "Anisotropic behaviours of massless Dirac fermions in graphene under periodic potentials", Nature Physics, vol. 4, pp. 213-217, Published Online: Feb. 24, 2008; doi:10.1038/nphys890.

B.M. Paschal; "Direct Submission", Submitted Oct. 19, 2007 Research Department, New England Biolabs, 240 County Road, Ipswich MA 10938, USA, 5 pages.

Sachdev S. Sidhu, et al; "High Copy Display of Large Proteins on Phage for Functional Selections", Journal of Molecular Biology, vol. 296, Dec. 13, 1999; pp. 487-495.

Zhuangchun Wu, et al; "Transparent, Conductive Carbon Nanotube Films", Science, vol. 305, Aug. 27, 2004, pp. 1273-1276.

Huanfen Yao, et al; "A contact lens with embedded sensor for monitoring tear glucose level", Biosensors and Bioelectronics, vol. 26, pp. 3290-3296; Available online Dec. 31, 2010.

Hyunjung Yi, et al "M13 Phage-Functionalized Single-Walled Carbon Nanotubes As Nanoprobes for Second Near-Infrared Window Fluorescence imaging of Targeted Tumors", NanoLetters, vol. 12, pp. 1176-1183; Published Jan. 23, 2012.

Michael B. Zwick, et al "The Maltose-Binding Protein as a Scaffold for Monovalent Display of Peptides Derived from Phage Libraries", Analytical Biochemistry, vol. 264, pp. 87-97, Article No. AB982793; Nov. 1, 1998.

USPTO RR dated Apr. 24, 2015 in connection with U.S. Appl. No. 14/171,898.

\* cited by examiner

SEQUENCE LISTING

```
<160> NUMBER OF SEQ ID NOS: 19

<210> SEQ ID NO 1
<211> LENGTH: 8
<212> TYPE: PRT
<213> ORGANISM: Artificial Sequence
<220> FEATURE:
<223> OTHER INFORMATION: peptide selectively binding to graphitic
      materials and volatile organic compounds
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (3)..(3)
<223> OTHER INFORMATION: X is W, Y, F or H
<220> FEATURE:
<221> NAME/KEY: VARIANT
<222> LOCATION: (6)..(6)
<223> OTHER INFORMATION: X is D, E, N or Q
<220> FEATURE:
<221> NAME/KEY: VARIANT
<222> LOCATION: (7)..(7)
<223> OTHER INFORMATION: X is I, L, or V

<400> SEQUENCE: 1

Xaa Ser Xaa Ala Ala Xaa Xaa Pro
1               5

<210> SEQ ID NO 2
<211> LENGTH: 8
<212> TYPE: PRT
<213> ORGANISM: Artificial Sequence
<220> FEATURE:
<223> OTHER INFORMATION: peptide selectively binding to graphitic
      materials and volatile organic compounds
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (2)..(2)
<223> OTHER INFORMATION: X is D, E, N, or Q
<220> FEATURE:
<221> NAME/KEY: VARIANT
<222> LOCATION: (4)..(4)
<223> OTHER INFORMATION: X is I, L, or V
<220> FEATURE:
<221> NAME/KEY: VARIANT
<222> LOCATION: (5)..(5)
<223> OTHER INFORMATION: X is D, E, N, or Q
<220> FEATURE:
<221> NAME/KEY: VARIANT
<222> LOCATION: (7)..(7)
<223> OTHER INFORMATION: X is I, L, or V

<400> SEQUENCE: 2

Xaa Xaa Pro Xaa Xaa Ala Xaa Pro
1               5

<210> SEQ ID NO 3
```

```
<211> LENGTH: 7
<212> TYPE: PRT
<213> ORGANISM: Artificial Sequence
<220> FEATURE:
<223> OTHER INFORMATION: peptide selectively binding to graphitic
      materials and volatile organic compounds
<220> FEATURE:
<221> NAME/KEY: VARIANT
<222> LOCATION: (2)..(2)
<223> OTHER INFORMATION: X is W, Y, F, or H
<220> FEATURE:
<221> NAME/KEY: VARIANT
<222> LOCATION: (5)..(5)
<223> OTHER INFORMATION: X is D, E, N, or Q
<220> FEATURE:
<221> NAME/KEY: VARIANT
<222> LOCATION: (6)..(6)
<223> OTHER INFORMATION: X is I, L, or V

<400> SEQUENCE: 3

Ser Xaa Ala Ala Xaa Xaa Pro
1               5

<210> SEQ ID NO 4
<211> LENGTH: 7
<212> TYPE: PRT
<213> ORGANISM: Artificial Sequence
<220> FEATURE:
<223> OTHER INFORMATION: peptide selectively binding to graphitic
      materials and volatile organic compounds
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (3)..(3)
<223> OTHER INFORMATION: X is I, L, or V
<220> FEATURE:
<221> NAME/KEY: VARIANT
<222> LOCATION: (4)..(4)
<223> OTHER INFORMATION: X is D, E, N, or Q
<220> FEATURE:
<221> NAME/KEY: VARIANT
<222> LOCATION: (6)..(6)
<223> OTHER INFORMATION: X is I, L, or V

<400> SEQUENCE: 4

Xaa Pro Xaa Xaa Ala Xaa Pro
1               5

<210> SEQ ID NO 5
<211> LENGTH: 8
<212> TYPE: PRT
<213> ORGANISM: Artificial Sequence
<220> FEATURE:
<223> OTHER INFORMATION: peptide selectively binding to graphitic
      materials and volatile organic compounds

<400> SEQUENCE: 5

Asp Ser Trp Ala Ala Asp Ile Pro
1               5

<210> SEQ ID NO 6
<211> LENGTH: 8
<212> TYPE: PRT
<213> ORGANISM: Artificial Sequence
<220> FEATURE:
<223> OTHER INFORMATION: peptide selectively binding to graphitic
      materials and volatile organic compounds

<400> SEQUENCE: 6
```

Asp Asn Pro Ile Gln Ala Val Pro
1               5

<210> SEQ ID NO 7
<211> LENGTH: 7
<212> TYPE: PRT
<213> ORGANISM: Artificial Sequence
<220> FEATURE:
<223> OTHER INFORMATION: peptide selectively binding to graphitic
      materials and volatile organic compounds

<400> SEQUENCE: 7

Ser Trp Ala Ala Asp Ile Pro
1               5

<210> SEQ ID NO 8
<211> LENGTH: 7
<212> TYPE: PRT
<213> ORGANISM: Artificial Sequence
<220> FEATURE:
<223> OTHER INFORMATION: peptide selectively binding to graphitic
      materials and volatile organic compounds

<400> SEQUENCE: 8

Asn Pro Ile Gln Ala Val Pro
1               5

<210> SEQ ID NO 9
<211> LENGTH: 7222
<212> TYPE: DNA
<213> ORGANISM: Artificial Sequence
<220> FEATURE:
<223> OTHER INFORMATION: cloning vector M13KE

<400> SEQUENCE: 9

| | | | | | |
|---|---|---|---|---|---|
| aatgctacta | ctattagtag | aattgatgcc | accttttcag | ctcgcgcccc | aaatgaaaat | 60 |
| atagctaaac | aggttattga | ccatttgcga | aatgtatcta | atggtcaaac | taaatctact | 120 |
| cgttcgcaga | attgggaatc | aactgttata | tggaatgaaa | cttccagaca | ccgtacttta | 180 |
| gttgcatatt | taaacatgt | tgagctacag | cattatattc | agcaattaag | ctctaagcca | 240 |
| tccgcaaaaa | tgacctctta | tcaaaaggag | caattaaagg | tactctctaa | tcctgacctg | 300 |
| ttggagtttg | cttccggtct | ggttcgcttt | gaagctcgaa | ttaaaacgcg | atatttgaag | 360 |
| tctttcgggc | ttcctcttaa | tctttttgat | gcaatccgct | ttgcttctga | ctataatagt | 420 |
| cagggtaaag | acctgatttt | tgatttatgg | tcattctcgt | tttctgaact | gtttaaagca | 480 |
| tttgaggggg | attcaatgaa | tatttatgac | gattccgcag | tattggacgc | tatccagtct | 540 |
| aaacatttta | ctattacccc | ctctggcaaa | acttcttttg | caaaagcctc | tcgctatttt | 600 |
| ggttttatc | gtcgtctggt | aaacgagggt | tatgatagtg | ttgctcttac | tatgcctcgt | 660 |
| aattcctttt | ggcgttatgt | atctgcatta | gttgaatgtg | gtattcctaa | atctcaactg | 720 |
| atgaatcttt | ctacctgtaa | taatgttgtt | ccgttagttc | gttttattaa | cgtagatttt | 780 |
| tcttcccaac | gtcctgactg | gtataatgag | ccagttctta | aaatcgcata | aggtaattca | 840 |
| caatgattaa | agttgaaatt | aaaccatctc | aagcccaatt | tactactcgt | tctggtgttt | 900 |
| ctcgtcaggg | caagccttat | tcactgaatg | agcagctttg | ttacgttgat | ttgggtaatg | 960 |
| aatatccggt | tcttgtcaag | attactcttg | atgaaggtca | gccagcctat | gcgcctggtc | 1020 |
| tgtacaccgt | tcatctgtcc | tctttcaaag | ttggtcagtt | cggttccctt | atgattgacc | 1080 |
| gtctgcgcct | cgttccggct | aagtaacatg | gagcaggtcg | cggatttcga | cacaatttat | 1140 |

```
caggcgatga tacaaatctc cgttgtactt tgtttcgcgc ttggtataat cgctgggggt    1200
caaagatgag tgttttagtg tattcttttg cctctttcgt tttaggttgg tgccttcgta    1260
gtggcattac gtattttacc cgtttaatgg aaacttcctc atgaaaaagt ctttagtcct    1320
caaagcctct gtagccgttg ctaccctcgt tccgatgctg tctttcgctg ctgagggtga    1380
cgatcccgca aaagcggcct ttaactccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaccga tacaattaaa ggctcctttt ggagcctttt    1560 tttttggagat tttcaacgtg aaaaaattat tattcgcaat tcctttagtg gtacctttct    1620
attctcactc ggccgaaact gttgaaagtt gtttagcaaa atcccataca gaaaattcat    1680
ttactaacgt ctggaaagac gacaaaactt tagatcgtta cgctaactat gagggctgtc    1740
tgtggaatgc tacaggcgtt gtagtttgta ctggtgacga aactcagtgt tacggtacat    1800
gggttcctat tgggcttgct atccctgaaa atgagggtgg tggctctgag ggtggcggtt    1860
ctgagggtgg cggttctgag ggtggcggta ctaaacctcc tgagtacggt gatacaccta    1920
ttccgggcta tacttatatc aaccctctcg acggcactta tccgcctggt actgagcaaa    1980
accccgctaa tcctaatcct tctcttgagg agtctcagcc tcttaatact ttcatgtttc    2040
agaataatag gttccgaaat aggcaggggg cattaactgt ttatacgggc actgttactc    2100
aaggcactga ccccgttaaa acttattacc agtacactcc tgtatcatca aaagccatgt    2160
atgacgctta ctggaacggt aaattcagag actgcgcttt ccattctggc tttaatgagg    2220
atttatttgt ttgtgaatat caaggccaat cgtctgacct gcctcaacct cctgtcaatg    2280
ctggcggcgg ctctggtggt ggttctggtg gcggctctga gggtggtggc tctgagggtg    2340
gcggttctga gggtggcggc tctgaggag gcggttccgg tggtggctct ggttccggtg    2400
attttgatta tgaaaagatg gcaaacgcta ataaggggc tatgaccgaa aatgccgatg    2460
aaaacgcgct acagtctgac gctaaaggca aacttgattc tgtcgctact gattacggtg    2520
ctgctatcga tggtttcatt ggtgacgttt ccggccttgc taatggtaat ggtgctactg    2580
gtgattttgc tggctctaat tcccaaatgg ctcaagtcgg tgacggtgat aattcacctt    2640
taatgaataa tttccgtcaa tatttacctt ccctccctca atcggttgaa tgtcgccctt    2700
ttgtctttgg cgctggtaaa ccatatgaat tttctattga ttgtgacaaa ataaacttat    2760
tccgtggtgt ctttgcgttt cttttatatg ttgccacctt tatgtatgta ttttctacgt    2820
ttgctaacat actgcgtaat aaggagtctt aatcatgcca gttcttttgg gtattccgtt    2880
attattgcgt ttcctcggtt tccttctggt aactttgttc ggctatctgc ttactttct    2940 taaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcattttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
```

```
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttctagt aattatgatt      3840 ccggtgttta ttcttattta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta atgtaatta attttgtttt cttgatgttt      4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg ctctaatct attagttgtt    4740 agtgctccta aagatatttt agataacctt cctcaattcc tttcaactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta tttttaatgg cgatgttta      4980 gggctatcag ttcgcgcatt aaagactaat agccattcaa aaatattgtc tgtgccacgt    5040
attcttacgc tttcaggtca aagggttct atctctgttg ccagaatgt tccttttatt      5100 actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg cgtaccgtt cctgtctaaa      5400 atccctttaa tcggcctcct gtttagctcc cgctctgatt ctaacgagga agcacgtta      5460 tacgtgctcg tcaaagcaac catagtacgg gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggttttc gccctttgac      5760 gttggagtcc acgttcttta atagtggact cttgttccaa actggaacaa cactcaaccc    5820
tatctcgggc tattcttttg atttataagg gattttgccg atttcggaac caccatcaaa    5880
```

```
caggattttc gcctgctggg gcaaaccagc gtggaccgct tgctgcaact ctctcagggc      5940
caggcggtga agggcaatca gctgttgccc gtctcactgg tgaaaagaaa aaccaccctg      6000
gcgcccaata cgcaaaccgc ctctccccgc gcgttggccg attcattaat gcagctggca      6060
cgacaggttt cccgactgga aagcgggcag tgagcgcaac gcaattaatg tgagttagct      6120
cactcattag gcaccccagg ctttacactt tatgcttccg gctcgtatgt tgtgtggaat      6180
tgtgagcgga taacaatttc acacaggaaa cagctatgac catgattacg ccaagcttgc      6240
atgcctgcag gtcctcgaat tcactggccg tcgttttaca acgtcgtgac tgggaaaacc      6300
ctggcgttac ccaacttaat cgccttgcag cacatccccc tttcgccagc tggcgtaata      6360
gcgaagaggc ccgcaccgat cgcccttccc aacagttgcg cagcctgaat ggcgaatggc      6420
gctttgcctg gtttccggca ccagaagcgg tgccggaaag ctggctggag tgcgatcttc      6480
ctgaggccga tactgtcgtc gtcccctcaa actggcagat gcacggttac gatgcgccca      6540
tctacaccaa cgtgacctat cccattacgg tcaatccgcc gtttgttccc acggagaatc      6600
cgacgggttg ttactcgctc acatttaatg ttgatgaaag ctggctacag gaaggccaga      6660
cgcgaattat ttttgatggc gttcctattg gttaaaaaat gagctgattt aacaaaaatt      6720
taatgcgaat tttaacaaaa tattaacgtt tacaatttaa atatttgctt atacaatctt      6780
cctgtttttg gggcttttct gattatcaac cggggtacat atgattgaca tgctagtttt      6840
acgattaccg ttcatcgatt ctcttgtttg ctccagactc tcaggcaatg acctgatagc      6900
ctttgtagat ctctcaaaaa tagctaccct ctccggcatt aatttatcag ctagaacggt      6960
tgaatatcat attgatggtg atttgactgt ctccggcctt tctcacccttt ttgaatcttt      7020 acctacacat tactcaggca ttgcatttaa aatatatgag ggttctaaaa attttatcc      7080 ttgcgttgaa ataaaggctt ctcccgcaaa agtattacag ggtcataatg ttttttggtac      7140 aaccgattta gctttatgct ctgaggcttt attgcttaat tttgctaatt ctttgccttg      7200
cctgtatgat ttattggatg tt                                              7222

<210> SEQ ID NO 10
<211> LENGTH: 41
<212> TYPE: DNA
<213> ORGANISM: Artificial Sequence
<220> FEATURE:
<223> OTHER INFORMATION: BamH I_SM_upper which is a primer used for
      site-directed mutation

<400> SEQUENCE: 10
aaggccgctt ttgcgggatc ctcaccctca gcagcgaaag a                          41

<210> SEQ ID NO 11
<211> LENGTH: 41
<212> TYPE: DNA
<213> ORGANISM: Artificial Sequence
<220> FEATURE:
<223> OTHER INFORMATION: BamH I_SM_lower which is a primer used for
      site-directed mutation

<400> SEQUENCE: 11
tctttcgctg ctgagggtga ggatcccgca aaagcggcct t                          41

<210> SEQ ID NO 12
<211> LENGTH: 90
<212> TYPE: DNA
<213> ORGANISM: Artificial Sequence
<220> FEATURE:
<223> OTHER INFORMATION: BamM13HK_P8_primer which is an extension
```

```
                    primer used for preparation

<400> SEQUENCE: 12
ttaatggaaa cttcctcatg aaaaagtctt tagtcctcaa agcctctgta gccgttgcta      60
ccctcgttcc gatgctgtct ttcgctgctg                                       90

<210> SEQ ID NO 13
<211> LENGTH: 95
<212> TYPE: DNA
<213> ORGANISM: Artificial Sequence
<220> FEATURE:
<223> OTHER INFORMATION: M13HK_P8 which is a library oligonucleotide
      used for preparation
<220> FEATURE:
<221> NAME/KEY: misc_feature
<222> LOCATION: (1)..(95)
<223> OTHER INFORMATION: n is a, g, c or t
<220> FEATURE:
<221> NAME/KEY: misc_feature
<222> LOCATION: (1)..(95)
<223> OTHER INFORMATION: m is a or c

<400> SEQUENCE: 13
aaggccgctt tgcgggatc cnnmnnmnnm nnmnnmnnmn nmncagcagc gaaagacagc       60
atcggaacga gggtagcaac ggctacagag gcttt                                 95

<210> SEQ ID NO 14
<211> LENGTH: 8
<212> TYPE: PRT
<213> ORGANISM: Artificial Sequence
<220> FEATURE:
<223> OTHER INFORMATION: P8GB#3

<400> SEQUENCE: 14

Asp Thr Lys Trp Thr Gly Gly Glu
1               5

<210> SEQ ID NO 15
<211> LENGTH: 8
<212> TYPE: PRT
<213> ORGANISM: Artificial Sequence
<220> FEATURE:
<223> OTHER INFORMATION: P8GB#6

<400> SEQUENCE: 15

Val Thr Ala Val Pro Asn Asp Thr
1               5

<210> SEQ ID NO 16
<211> LENGTH: 4
<212> TYPE: PRT
<213> ORGANISM: Artificial Sequence
<220> FEATURE:
<223> OTHER INFORMATION: P8GB#8
<220> FEATURE:
<221> NAME/KEY: misc_feature
<222> LOCATION: (4)..(4)
<223> OTHER INFORMATION: Xaa can be any naturally occurring amino acid

<400> SEQUENCE: 16

Glu Gly Glu Xaa
1

<210> SEQ ID NO 17
<211> LENGTH: 97
<212> TYPE: DNA
<213> ORGANISM: Artificial Sequence
```

```
<220> FEATURE:
<223> OTHER INFORMATION: insert for coding a peptide having binding
      affinity to graphitic materials

<400> SEQUENCE: 17
catgaaaaag tcttttgtcc tcaaagcctc tgtagccgtt gctaccctcg ttccgatgct        60
gtctttcgct gctgattctt gggctgcgga tattccg                                97

<210> SEQ ID NO 18
<211> LENGTH: 97
<212> TYPE: DNA
<213> ORGANISM: Artificial Sequence
<220> FEATURE:
<223> OTHER INFORMATION: insert for coding a peptide having binding
      affinity to graphitic materials

<400> SEQUENCE: 18
gatccggaat atccgcagcc caagaatcag gcagcgaaag acagcatcgg aacgagggta        60
gcaacggcta cagaggcttt gaggacaaag acttttt                                97

<210> SEQ ID NO 19
<211> LENGTH: 50
<212> TYPE: PRT
<213> ORGANISM: P8 protein of M13 phage

<400> SEQUENCE: 19

Ala Glu Gly Asp Asp Pro Ala Lys Ala Ala Phe Asn Ser Leu Gln Ala
1               5                   10                  15

Ser Ala Thr Glu Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45

Ala Ser
    50
```

PEPTIDE SELECTIVELY BINDING TO GRAPHITIC MATERIALS AND VOLATILE ORGANIC COMPOUNDS

CROSS-REFERENCE TO RELATED APPLICATION

This application claims the benefit of Korean Patent Application No. 10-2013-0041173, filed on Apr. 15, 2013, in the Korean Intellectual Property Office, the disclosure of which is incorporated herein in its entirety by reference.

BACKGROUND

1. Field

The present disclosure relates to a novel peptide specifically binding to graphitic materials.

2. Description of the Related Art

Recently, researches are actively carried out on utilization of the superior electrical, thermal, optical and mechanical properties of low-dimensional carbon materials such as graphene, carbon nanotube, etc. in various applications.

In general, permanent modification of the surface of nanocarbon materials through chemical reactions is employed for modification of their properties. However, if the surface is permanently modified through chemical reaction, the intrinsic properties of the low-dimensional carbon materials such as high electrical conductivity are greatly deteriorated.

Accordingly, there is an increasing need of a novel method capable of providing various functionalities without disrupting the superior properties of nanocarbon materials.

In this regard, molecular recognition is a method of binding to a desired substance without chemical reaction utilizing the selectivity of a biomaterial and can be found in nature, for example, in the binding between complementary DNA sequences, antigen-antibody interaction, etc. Recently, researches are actively conducted on modification of the surface of nanocarbon materials with minimized deterioration of their properties using peptides that specifically bind to the nanocarbon materials through molecular recognition.

Most of the current researches on functionalization of carbon nanotube, etc. using peptides are based on the commercially available p3 peptide library (Fabricating genetically engineered high-power lithium-ion batteries using multiple virus genes, Yun Jung Lee et al., Science Vol. 324, 2009 May 22.). However, examples of the functionalization of a nanocarbon material using actually discovered peptides are already reported in a biosensor, but their applications are also very limited. It is because a synergic effect between the peptides cannot be expected since, although a large quantity of peptides are needed to functionalize the nanocarbon material, the peptides are small in size. In addition, since the peptides derived from the p3 peptide library are present at small copy number of about 5 on the tip of phage particles, it is difficult to functionalize the nanocarbon material using the phages to which the peptides are bound.

REFERENCES OF THE RELATED ART

Non-Patent Document

Fabricating genetically engineered high-power lithium-ion batteries using multiple virus genes (Yun Jung Lee et al., Science Vol. 324, 2009 May 22.)

SUMMARY

An aspect provides a peptide or a peptide set including one or more selected from the group consisting of amino acid sequences of $X_2SX_1AAX_2X_3P$ (SEQ ID NO: 1), $X_2X_2PX_3X_2AX_3P$ (SEQ ID NO: 2), $SX_1AAX_2X_3P$ (SEQ ID NO: 3) and $X_2PX_3X_2AX_3P$ (SEQ ID NO: 4).

Another aspect provides a phage in which the peptide or the peptide set is displayed on a coat protein of the phage or a fragment thereof.

Still another aspect provides a graphitic material on which the peptide or peptide set or the phage is bound.

Still another aspect provides a device for detecting or eliminating a volatile organic compound, including a substrate on which the peptide or peptide set or the phage is immobilized.

Still another aspect provides a method of detecting or eliminating a volatile organic compound present in a sample, including contacting the sample with the peptide or peptide set or the phage.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
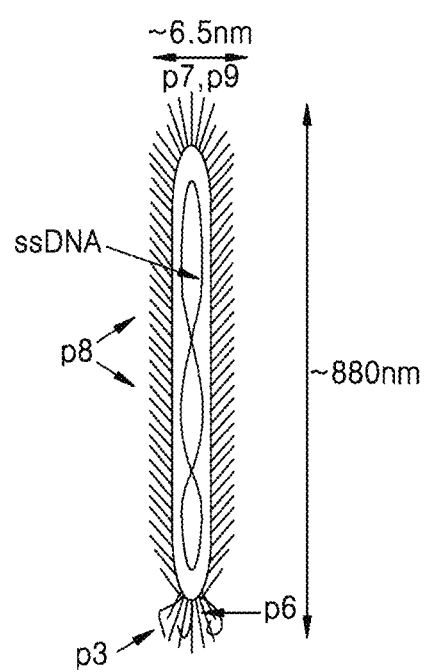
FIG. 1 is a schematic illustration showing a structure of M13 phage according to a specific embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the exemplary embodiments are merely described below, by referring to the figures, to explain aspects of the present description.

An aspect provides a peptide or a peptide set including one or more selected from the group consisting of amino acid sequences of $X_2SX_1AAX_2X_3P$ (SEQ ID NO: 1), $X_2X_2PX_3X_2AX_3P$ (SEQ ID NO: 2), $SX_1AAX_2X_3P$ (SEQ ID NO: 3) and $X_2PX_3X_2AX_3P$ (SEQ ID NO: 4).

Further, the peptide or peptide set may be a peptide or peptide set including one or more selected from the group consisting of amino acid sequences of SEQ ID NOs: 5 to 8.

Consecutive amino acid sequences of a coat protein of a phage may be linked to the N-terminus or C-terminus of the amino acid sequence of the peptide or peptide set. Therefore, for example, the peptide or peptide set may have an amino acid sequence having a length of 5 to 60, 7 to 55, 7 to 40, 7 to 30, 7 to 20, or 7 to 10 amino acids.

The peptide may have a conservative substitution of a known peptide. As used herein, the term "conservative substitution" denotes replacement of a first amino acid residue by a second different amino acid residue without changing biophysical properties of a protein or a peptide. Here, the first and second amino acid residues mean those having side chains having similar biophysical properties. The similar biophysical properties may include an ability to donate or accept hydrophobicity, charge, polarity, or hydrogen bonding. Examples of the conservative substitution may be within the groups of basic amino acids (arginine, lysine, and histidine), acidic amino acids (glutamic acid and aspartic acid), polar amino acids (glutamine and asparagine), hydrophobic amino acids (leucine, isoleucine, valine and methionine), hydrophilic amino acids (aspartic acid, glutamic acid, asparagine and glutamine), aromatic amino acids (phenylalanine, tryptophan, tyrosine and histidine), and small amino acids (glycine, alanine, serine and threonine). Amino acid substitutions that do not generally alter specific activity are known in the art. For example, in the peptide, $X_1$ may be W, Y, F or H, $X_2$ may be D, E, N or Q, and $X_3$ may be I, L or V.

Another aspect provides a phage in which the peptide or the peptide set including one or more selected from the group consisting of amino acid sequences of $X_2SX_1AAX_2X_3P$ (SEQ ID NO: 1), $X_2X_2PX_3X_2AX_3P$ (SEQ ID NO: 2), $SX_1AAX_2X_3P$ (SEQ ID NO: 3) and $X_2PX_3X_2AX_3P$ (SEQ ID NO: 4) is displayed on a coat protein of the phage or a fragment thereof.

The peptide or peptide set is the same as described above.

The term "phage" or "bacteriophage" is used interchangeably, and may refer to a virus that infects bacteria and replicates within the bacteria. The phage or bacteriophage may be used to display a peptide which selectively or specifically binds to a graphitic material or volatile organic compound. The phage may be genetically engineered to display the peptide capable of binding to the graphitic material on a coat protein of the phage or a fragment thereof. As used herein, the term "genetic engineering" or "genetically engineered" means introduction of one or more genetic modifications into the phage in order to display the peptide capable of binding to the graphitic material on the coat protein of the phage or the fragment thereof, or a phage prepared thereby. The genetic modifications include introduction of a foreign gene encoding the peptide. The phage may be a filamentous phage, for example, M13 phage, F1 phage, Fd phage, If1 phage, Ike phage, Zj/Z phage, Ff phage, Xf phage, Pf1 phage, or Pf3 phage.

As used herein, the term "phage display" may refer to display of a functional foreign peptide or protein on the surface of a phage or phagemid particle. The surface of the phage may refer to a coat protein of the phage or a fragment thereof. Further, the phage may be a phage in which the C-terminus of the functional foreign peptide is linked to the N-terminus of the coat protein of the phage, or the peptide is inserted between consecutive amino acid sequences of the coat protein of the phage or replaced for a part of the consecutive amino acid sequences of the coat protein. The positions in the amino acid sequence of the coat protein, at which the peptide is inserted or replaced, may be positions of 1 to 5, positions of 1 to 40, positions of 1 to 30, positions of 1 to 20, position of 1 to 10, positions of 2 to 8, positions of 2 to 4, positions of 2 to 3, positions of 3 to 4, or a position of 2 from the N-terminus of the coat protein. Further, the coat protein may be p3, p6, p8 or p9. For example, the C-terminus of any one peptide of SEQ ID NO: 1 to SEQ ID NO: 8 may be linked to the body of M13 phage, that is, not to the tip of the phage, but to the N-terminus of p8 (SEQ ID NO: 19) having a length of 50 amino acids, which is present on the body in a longitudinal direction. Further, for example, any one peptide of SEQ ID NO: 1 to SEQ ID NO: 8 may be replaced for the positions of 2 to 4 (e.g., EGD), the positions of 2 to 3 or 3 to 4, or the position of 2 in the amino acid sequence of the coat protein p8 of M13 phage.

Another aspect provides a graphitic material, to which the peptide or peptide set including one or more selected from the group consisting of amino acid sequences of $X_2SX_1AAX_2X_3P$ (SEQ ID NO: 1), $X_2X_2PX_3X_2AX_3P$ (SEQ ID NO: 2), $SX_1AAX_2X_3P$ (SEQ ID NO: 3) and $X_2PX_3X_2AX_3P$ (SEQ ID NO: 4), or the peptide-displaying phage is bound.

The peptide or peptide set, and the phage are the same as described above.

As used herein, the term "graphitic material" may refer to a material having a graphitic surface with hexagonal arrangement of carbon atoms. The graphitic material may include any graphitic material having the graphitic surface, regardless of physical, chemical or structural properties. Examples of the graphitic material may include materials having a surface with hexagonal arrangement of carbon atoms, such as graphite, graphene, highly ordered pyrolytic graphite (HOPG), carbon nanotube, fullerene, etc.

The peptide binding to the graphitic material may be selected from peptide libraries, for example, by a phage display technique. Through the phage display technique, the peptide may be genetically linked to, inserted into, or substituted for the coat protein of the phage, resulting in display of the protein on the exterior of phage, in which the peptide may be encoded by genetic information in the virion. Vast numbers of variants of the protein may be selected and screened by the displayed protein and DNA encoding the same, this method is called "biopanning". Briefly, biopanning is carried out by incubating the pool of phage-displayed variants with a target (e.g., graphitic material) that has been immobilized, washing away unbound phage, and eluting specifically bound phage by disrupting the binding interactions between the phage and the target. A portion of the eluted phage is set aside for DNA sequencing and peptide identification, and the remainder is amplified in vivo to prepare a sub-library for the next round. Then, this procedure is repeated.

Therefore, the present invention provides a method of selecting peptides binding to the graphitic surface, including: providing a peptide-displaying phage library; reacting the phage library with the graphitic material; removing phages that are unbound in the reaction; and selecting phages that bind to the graphitic material from the phage library; and further including: amplifying the selected phages in a host cell to repeat the above procedure, and isolating amplified or replicated phages, or expressed peptides.

In the method of selecting the peptide binding to the graphitic material, the phage may be M13 phage, F1 phage, Fd phage, If1 phage, Ike phage, Zj/Z phage, Ff phage, Xf phage, Pf1 phage or Pf3 phage, and the peptide library may be, for example, p8 peptide library of M13 phage.

In a specific embodiment, since a phage has about 2700 copies of the p8 protein, the p8 peptide library may be efficiently amplified, and no additional protein purification process is needed.

After selecting the peptide specifically binding to the graphitic material, it is possible to prepare the graphitic material, on which the peptide itself or the phage displaying the peptide on its coat protein or a fragment thereof is bound.

A method of preparing the graphitic material on which the peptide itself or the peptide-phage displaying is bound may be a dialysis method, a dip coating method, a spin coating method, a dropping method, a gravure printing method, a screening printing method, a letterpress method, a die coating method, a curtain coating method, an ink jet method, a spray coating method, a sputtering method, or a vacuum deposition method. The dip coating method may include preparing a phage solution by adding the peptide-displaying phage according to an exemplary embodiment to a solution (e.g., distilled water, PBS, TBS); and dipping graphitic materials in the phage solution. In addition, the dialysis method may include carrying out dialysis of graphitic materials against surfactant-containing distilled water to prepare a colloid solution; and mixing the colloid solution with the phage solution at a predetermined molar ratio in a container having a semipermeable membrane, followed by dialysis.

In the preparation method, as pH of the solvent used in the phage solution is increased, electrostatic repulsion between the phages may increase to increase the distance between the phages. In addition, as the concentration of the phage is increased, the distance between the phages arranged on the graphitic material may become closer. Therefore, those skilled in the art may control the number of and the distance between the phages which are arranged on the graphitic material by controlling pH and concentration of the phage, if necessary.

In the dialysis method, the colloid solution may be an aqueous solution, in which graphitic materials are dispersed or dissolved. The colloid solution may be prepared by stabilizing the graphitic materials in the surfactant-containing solution. The surfactant may stabilize the graphitic material and may be a surfactant having affinity to the peptide or the phage. Example of the surfactant may include sodium cholate, SDS (sodium dodecyl sulfate), DOC (sodium deoxycholate). Further, those skilled in the art may control the mixing molar ratio of the colloid materials and the phage solution according to desired properties.

If the graphitic material is a graphene sheet or a carbon nanotube, the graphitic material may have a sheet form. In addition, the internal structure of the graphitic material may have a percolated network structure. As used herein, the term "percolated network" may refer to a lattice structure consisting of random conductive or non-conductive linkages. If the graphitic material is in the form of sheet, the sheet may have, for example, a thickness of 40 to 350 nm and an area of 0.001 to 1000 $cm^2$.

In a specific embodiment, the peptide may specifically bind to the graphitic material, and thus additional functionalities may be provided by a non-destructive method of causing no damage to the properties of the graphitic material. If the peptide is displayed on the coat protein of the filamentous phage, a contact area with the graphitic material is large to provide a stronger binding affinity.

In another specific embodiment, the phage may be arranged on the graphitic surface with directionality using the filamentous structure of the phage itself. For example, it may be arranged in a row in a specific direction. In this case, the binding affinity of the peptide present on the coat protein of the phage for the graphitic surface is enhanced and the phage is arranged in a row. The phage arranged in a row may provide anisotropic functionality to the graphitic surface. In addition to the arrangement in a row, the phage may be arranged to form a structure having specific directionality, such as a layered (e.g., smectic), nematic, spiral or lattice structure. Accordingly, various functionalities may be provided onto the graphitic surface using the arrangement structures of the phage.

Still another aspect provides a composition of detecting or eliminating a volatile organic compound, including the peptide or peptide set which includes one or more selected from the group consisting of amino acid sequences of $X_2SX_1AAX_2X_3P$ (SEQ ID NO: 1), $X_2X_2PX_3X_2AX_3P$ (SEQ ID NO: 2), $SX_1AAX_2X_3P$ (SEQ ID NO: 3) and $X_2PX_3X_2AX_3P$ (SEQ ID NO: 4).

The peptide or peptide set may be those displayed on the coat protein of the phage or the fragment thereof. The peptide or peptide set, or the phage may be those bound to the graphitic material. The peptide, phage and graphitic material are the same as described above.

As used herein, the term "volatile organic compound" may refer to a liquid, gas, or solid organic compound that is continuously volatilized and discharged into the air at a predetermined temperature and pressure, and may include organic compounds that exist as gases at a room temperature or atmospheric pressure, such as hydrocarbons composed of carbon and hydrogen, halogenated hydrocarbons, or nitrogen- or sulfur-containing hydrocarbons.

The volatile organic compound may be hydrocarbons containing aromatic groups. The hydrocarbons containing aromatic groups may be hydrocarbons containing benzene rings. The hydrocarbons containing benzene rings may be hydrocarbons, in which at least one hydrogen atom of the benzene is substituted by $C_1$ to $C_{10}$ alkyl group, alkenyl group, or alkynyl group. Further, the hydrocarbons containing benzene rings may be $C_6$ to $C_7$ hydrocarbons.

Examples of the volatile organic compound may include acetaldehyde, acetylene, acetylene dichloride, acrolein, acrylonitrile, benzene, 1,3-butadiene, butane, 1-butene, 2-butene, carbon tetrachloride, chloroform, cyclohexane, 1,2-dichloroethane, diethylamine, dimethylamine, ethylene, formaldehyde, n-hexane, isopropyl alcohol, methanol, methyl ethyl ketone, methylene chloride, MTBE, propylene, propyleneoxide, 1,1,1-trichloroethane, trichloroethylene, gasoline, naphtha, crude oil, acetic acid, ethylbenzene, nitrobenzene, toluene, tetrachloroethylene, xylene or styrene.

In a specific embodiment, the peptide including the amino acid sequence of SEQ ID NO: 1 or SEQ ID NO: 3, more particularly, the amino acid sequence of SEQ ID NOs: 5 or 7 according to an exemplary embodiment may selectively bind to benzene among the volatile organic compounds. Further, the peptide including the amino acid sequence of SEQ ID NO: 2 or SEQ ID NO: 4, more particularly, the amino acid sequence of SEQ ID NOs: 6 or 8 according to an exemplary embodiment may selectively bind to toluene among the volatile organic compounds.

Still another aspect provides a device for detecting or eliminating a volatile organic compound, including the peptide or peptide set.

The detecting or eliminating device may further include a substrate. The peptide or peptide set according to an exemplary embodiment may be immobilized onto the substrate. Further, the detecting or eliminating device may include a substrate onto which the phage displaying the peptide or peptide set according to an exemplary embodiment on the coat protein of the phage or the fragment thereof, or the graphitic material bound with the peptide or peptide set or the phage is immobilized or coated.

The substrate may be a conductive substrate or an insulating substrate. In some embodiments, the substrate may be an insulating substrate with at least one electrode thereon. The at least one electrode may include a first electrode, a second electrode, or a third electrode. In some embodiments, the at least one electrode may include a working electrode, an opposite electrode, or a reference electrode. The at least one electrode may further include, in addition to the working electrode, the opposite electrode, and the reference electrode, an auxiliary electrode and a recognition electrode. In a case in which a graphitic material, to which the peptide or phage is bound, is disposed on an insulating substrate with at least one electrode thereon, the graphitic material may be disposed on a first electrode, or a working electrode, or a part thereof.

Examples of the substrate may include a silver substrate, a silver epoxy substrate, a palladium substrate, a copper substrate, a gold substrate, a platinum substrate, a silver/silver chloride substrate, a silver/silver ion substrate, a mercury/mercury oxide substrate, a conductive carbon substrate, a semiconductor substrate, an oxide substrate, and a polymer substrate.

The substrate may be also a transparent flexible substrate. Examples of the transparent flexible substrate may include substrates that are manufactured from polydimethylsiloxane, PDMS), polyethersulfone (PES), poly(3,4-ethylenedioxythiophene), poly(styrenesulfonate), polyimide, polyurethane, polyester, perfluoropolyether (PFPE), polycarbonate, or combinations thereof.

Figure 12:
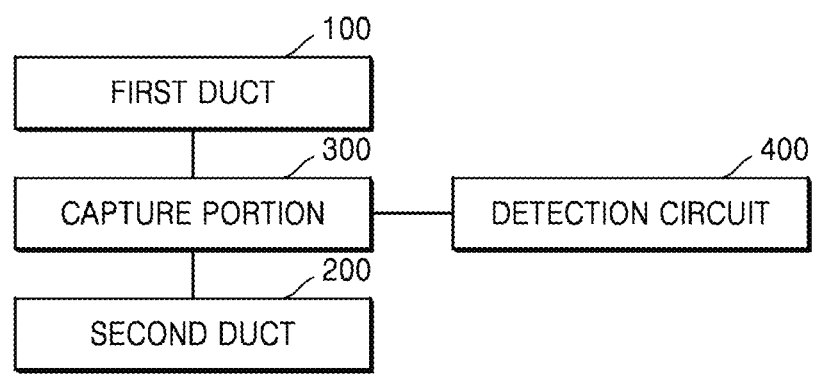
FIG. 12 is a schematic illustration showing a structure of a device for detecting or eliminating volatile organic compounds according to a specific embodiment.

Referring to FIG. 12, the device for detecting or eliminating a volatile organic compound may include a first duct 100, a second duct 200, and an capture portion 300.

The first duct 100 has a flow channel therein through which a sample enters. The first duct 100 may be a micro channel or a micro flow channel. The first duct 100 may include a first tube, a second tube, or a third tube, and the first tube may be connected to, for example, a facility or the mouth of an animal, through which the sample enters. The sample may be air or a liquid. The second tube may be connected to a rear end of the first tube, and the third tube may be connected to a rear end of the second tube. The third tube may include a first portion having a diameter equal to that of the second tube, and a second portion that is conical such that the diameter thereof gradually increases toward a read end thereof.

The device may include a pre-treatment portion that may be either located inside or connected to the first duct 100. The capture portion 300 may be disposed on the rear side of the first duct 100. The pre-treatment portion may be used to regulate the moisture of a sample entering the first duct 100 or remove dust. An example of the pre-treatment portion may include a moisture supply portion configured to supply moisture into the first duct 100, a moisture sensor configured to measure the moisture of a sample passing through the first duct 100, or a filter configured to remove dust included in contaminated air. The filter may be used to remove a solid component or a foreign material included in the sample, and may be a fibrous filter.

The capture portion 300 may detect or remove a volatile organic compound, and may include a sensor including a substrate on which the peptide or peptide set, or the phage is immobilized.

Figure 13:
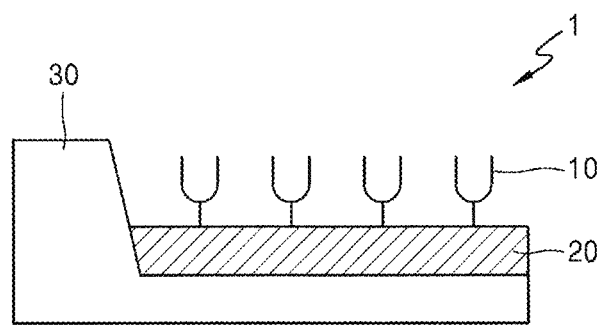
FIG. 13 is a schematic illustration showing a sensor of the device for detecting or eliminating volatile organic compounds according to a specific embodiment.

Referring to FIG. 13, an example of an capture portion may be a cantilever sensor 30. In this regard, a volatile organic compound binding layer 10, for example, a peptide or phage according to an embodiment may be immobilized on the cantilever sensor 30 through a substrate 20. The substrate 20 is already described above. The cantilever sensor 30 may be in a dynamic mode in which change in a resonance frequency number expressed by the change in mass and spring constant is measured, or a static mode in which a displacement that occurs due to the change in surface stress caused by a specific reaction on a cantilever sensor is measured. The cantilever sensor 30 may further include a circuit that measures a warp phenomenon or the change in resonance frequency number of the sensor, a piezoelectric sensor that converts a state of the cantilever sensor 30 that has been changed due to vibrations into an electric sensing signal, or a circuit that measures the change in a unique vibration number of the cantilever sensor 30 through the electric sensing signal.

During a sample passes through the capture portion 300, a volatile organic compound included in the sample may be detected by the detection circuit 400. The term "detection of a volatile organic compound" used herein may include qualitative, semi-quantitative, and quantitative detections of a volatile organic compound included in a sample. Qualitative evaluation results show whether a volatile organic compound is detected in a sample. Semi-quantitative evaluation results show whether an amount of a volatile organic compound included in a sample is equal to or greater than a certain boundary level. Quantitative evaluation results show a positive numeral indication of a volatile organic compound included in a sample.

The second duct 200 is connected to the rear side of the capture portion 300. The second duct 200 may be a micro channel or a micro flow channel. The second duct 200 may include a fourth tube and a fifth tube. The fourth tube may have a structure that is symmetric to that of the third tube. That is, the fourth tube may include a third portion having a diameter equal to that of the second portion; a fourth portion that is formed at a rear end of the third portion and conical such that the diameter thereof gradually decreases toward the read end thereof; and a fifth portion that is formed on a read end of the fourth portion.

The fifth tube is connected to the fifth portion of the fourth tube, extending in a certain length. A ventilation fan may be installed at the fifth portion. The ventilation fan may be connected to a motor installed outside the second duct 200. Due to the ventilation fan, the sample enters the first duct 100 and is discharged to the outside through the second duct 200. In this regard, the volatile organic compound in the sample may be detected or eliminated while passing through the capture portion 300.

Still another aspect provides a method of detecting or eliminating a volatile organic compound present in a sample, including contacting the sample with the peptide or peptide set or the phage.

The detecting method may include providing the sample to be analyzed; contacting the sample with the peptide or peptide set, the phage, or the graphitic material; or detecting a volatile organic compound-peptide complex present in the sample from the contacted sample.

Further, the eliminating method may include providing the sample to be analyzed; contacting the sample with the peptide or peptide set, the phage, or the graphitic material; or eliminating the volatile organic compound-peptide complex present in the sample from the contacted sample, after formation of the complex.

The sample to be analyzed may be a sample suspected of containing the volatile organic compound, and may include a liquid, air, or human exhaled breath.

The contacting is to bind the volatile organic compound present in the sample with the peptide or the peptide set, and to mix the peptide or peptide set with the sample. The mixing may be performed by applying the sample to the substrate, onto which the peptide or peptide set is immobilized. Further, the mixing may be performed in a liquid medium or the air. The liquid medium may include a buffer, a solvent or distilled water.

The detecting is to detect the presence or absence of the volatile organic compound in the sample, and it may be performed to detect the volatile organic compound in the sample, qualitatively, semi-quantitatively, and quantitatively. The detecting may be performed by an electrochemical, optical, or mass spectrometric method. The detecting by the electrochemical method may include sensing and measuring the electron transfer which occurs before and after contacting of the sample with the peptide, that is, before and after binding of the volatile organic compound with the peptide. The detecting by the optical method may include labeling the peptide with a fluorescent material to measure fluorescence of the volatile organic compound-peptide complex. The detecting by the mass spectrometric method may include analyzing a difference in the mass spectra acquired before and after contacting of the sample with the peptide, that is, before and after binding of the volatile organic compound with the peptide.

The composition, device or method of detecting the volatile organic compound according to an exemplary embodiment may be used to detect the presence or absence of the volatile organic compounds present in human exhaled breath, thereby being utilized as a sensor for diagnosing diseases. For example, volatile organic compounds (e.g., benzene or toluene, etc.) are detected in exhaled breath of patients with lung cancer. Therefore, the composition, device or method of detecting the volatile organic compound according to an exemplary embodiment may be applied to a diagnostic sensor for diseases, for example, a diagnostic kit for lung cancer, a diagnostic sensor for lung cancer, or a diagnostic method for lung cancer.

EFFECTS OF THE INVENTION

A peptide according to an aspect, and a phage displaying the peptide have excellent binding affinity of specifically binding to a graphitic material, and provide various functionalities onto the graphitic material in a non-destructive, economic manner.

The peptide according to another aspect has excellent selectivity for volatile organic compounds and is stable at room temperature, thereby effectively detecting or eliminating volatile organic compounds present in the air.

Hereinafter, the present invention will be described in more detail with reference to Examples. However, these Examples are for illustrative purposes only, and the invention is not intended to be limited by these Examples.

Example 1. Screening of Peptides Selectively Binding to Graphitic Materials

1. Preparation of M13 Phage-Display p8 Peptide Library

An M13 phage-display p8 peptide library is prepared in order to select peptides selectively binding to graphitic materials.

First, an M13HK vector is prepared using oligonucleotides of SEQ ID NOs: 10 and 11 for site-directed mutation of the $1381^{st}$ base pair C of an M13KE vector (NEB, product#N0316S) (SEQ ID NO: 9) to G. The prepared M13HK vector is double-digested using restriction enzymes, BspHI (NEB, product# R0517S) and BamHI (NEB, product#R3136T), and dephosphorylated using antarctic phosphatase. The dephosphorylated vector is ligated to a double-digested DNA duplex by incubation at 16° C. overnight. A product is then purified and concentrated. Electorcompetent cells (XL-1 Blue, Stratagene) are transformed with 2 µl of a concentrated ligated vector solution by electroporation at 18 kV/cml. A total of five transformations are performed for the library construction. Then, the transformed cells are incubated for 60 minutes, and fractions of several transformants are plated onto agar plates containing x-gal/isopropyl-β-D-1-thiogalactopyranoside (IPTG)/tetracycline (Tet) to determine the diversity of the library. The remaining cells are amplified in a shaking incubator for 8 hours. Oligonucleotides of SEQ ID NOs: 12 and 13 are used in construction of the phage-display p8 peptide library.

The base sequences of the phage-display p8 peptide library constructed according to an exemplary embodiment have diversity of $4.8 \times 10^7$ pfu (plaque forming unit), and include approximately $1.3 \times 10^5$ copies of each sequence.

FIG. 1 is a schematic illustration showing a structure of M13 phage according to a specific embodiment.

As shown in FIG. 1, M13 phage has a length of about 880 nm and a diameter of about 6.5 nm, and consists of single stranded DNA of 6407 nucleotides, which is wrapped by the major coat protein of p8 protein (50 amino acid residues) with 2700 copies, and the minor coat proteins of p3 (427 amino acid residues), p6 (112 amino acid residues), p7 (33 amino acid residues), and p9 (32 amino acid residues) with 5 copies or smaller. The peptide library according to an exemplary embodiment displays by replacement of the amino acid sequence at positions of 2 to 4 (i.e., EGD) of p8.

As described above, when the phage-display p8 peptide library is used, it is easy to amplify the p8 coat protein using the phage because the p8 coat protein has high copy numbers of about 2700. Therefore, no additional protein purification process is needed, and the cost of peptide production is reduced. Further, since p8 coat protein is present on the body of the M13 phage, the area where the peptide can be displayed is relatively very large. Further, since the phage has a filamentous structure, it may provide strong binding affinity of binding to a graphitic material, owing to large contact area of the peptide.

2. Screening of Peptide

The phage-display p8 peptide library prepared in 1 of Example 1 is used to screen peptides binding to graphene by a bio-panning method.

First, a highly ordered pyrolytic graphite (HOPG) substrate (manufacturer: SPI product#439HP-AB) having a diameter of 1 cm is prepared. In this regard, the HOPG substrate is a HOPG substrate having a relatively large grain size of 100 μm or smaller. Previously, a carbon nanotube film surface damaged during its production process has been generally used as a graphitic surface, and thus it is difficult to identify peptides having high binding affinity. In order to solve this problem, a fresh surface is detached from HOPG as a material having a graphitic surface using a tape immediately before use, so as to minimize the defect of the sample surface due to, for example, oxidation. Subsequently, the phage display p8 peptide library of $4.8 \times 10^{10}$ pfu ($4.8 \times 10^7$ diversities, 1000 copies per each sequence) prepared in 1 of Example 1 is prepared in 100 μL of Tris-buffered saline (TBS) and conjugated with the HOPG surface for 1 hour in a shaking incubator at 100 rpm. 1 hour later, the solution is removed and the surface is washed 10 times in TBS. The washed HOPG surface is reacted with Tris-HCl of pH 2.2 as an acidic buffer for 8 minutes to elute peptides reacting non-selectively, and the remaining phage was eluted with an XL-1 blue *E. coli* culture in mid-log phase for 30 minutes. A portion of the eluted culture is set aside for DNA sequencing and peptide identification, and the remainder is amplified to prepare a sub-library for the next round. The above procedure is repeated using the prepared sub-library. Meanwhile, the left plaque is subjected to DNA sequencing to obtain the p8 peptide sequence, and the sequence is analyzed to obtain 4 peptide sequences that react with the graphitic surface, which are given in the following Table 1, together with a negative control group.

TABLE 1

| SEQ ID NO. | Amino acid sequence |
|---|---|
| P8GB#1 (SEQ ID NO. 5) | DSWAADIP |
| P8GB#3 (SEQ ID NO. 14) | DTKWTGGE |
| P8GB#5 (SEQ ID NO. 6) | DNPIQAVP |
| P8GB#6 (SEQ ID NO. 15) | VTAVPNDT |
| P8GB#8 (M13HK, negative control, SEQ ID NO. 16) | EGE |

3. Comparison of Binding Affinity

The following experiment is conducted to compare the binding affinity of the peptide sequences, p8 GB#1, 3, 5, 6 and 8 screened in 2 of Example 1 for the graphitic surface.

First, M13 phages each including the peptide sequences p8 GB#1, 3, 5, 6 and 8 are prepared according to the biopanning method used in 2 of Example 1 and, after conjugating them with HOPG under the same conditions, binding affinity is compared by counting the number of phages remaining after washing. That is, each of the five peptide sequences is prepared in 100 μL of TBS buffer and conjugated with the HOPG surface for 1 hour in a shaking incubator at 100 rpm. 1 hour later, the solution is removed and the surface was washed 10 times in TBS. The washed HOPG surface is reacted with Tris-HCl of pH 2.2 as an acidic buffer for 8 minutes to elute peptides reacting non-selectively, and the remaining phage is eluted with an XL-1 blue *E. coli* culture in mid-log phase for 30 minutes. Each number of 5 peptide sequences in the eluted culture is counted by tittering. The result is shown in a graph of FIG. 2.

Figure 2:
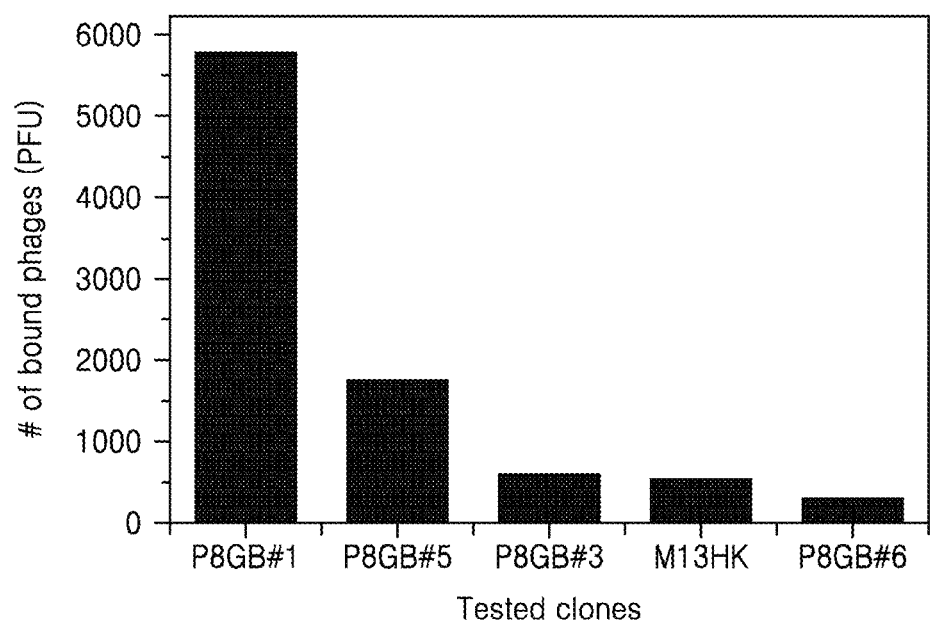
FIG. 2 shows an experimental result of comparing binding affinity of a peptide according to an exemplary embodiment for graphitic surface.

FIG. 2 shows an experimental result of comparing binding affinity of the peptide according to an exemplary embodiment for graphitic surface.

As shown in FIG. 2, p8 GB#1 (SEQ ID NO: 5) according to an exemplary embodiment shows about 9.6 times stronger binding affinity and p8 GB#5 (SEQ ID NO: 6) shows about 2.9 times stronger binding affinity, as compared to p8 GB#8 (M13HK, negative control). This result indicates that the peptide according to an exemplary embodiment has very higher binding affinity than peptides of other sequences derived from the same M13 phage display p8 peptide library.

Further, the result of comparing the binding affinity implies that aspartic acid, the first amino acid residue of P8 GB#1 and P8 GB#5, does not greatly influence on binding affinity. Thus, GP1 (SEQ ID NO: 7) and GP2 (SEQ ID NO: 8) are prepared by deleting the above amino acid, and their binding affinity for graphitic surface is also compared with the control group in the same manner as above. The result is shown in a graph of FIG. 3.

Figure 3:
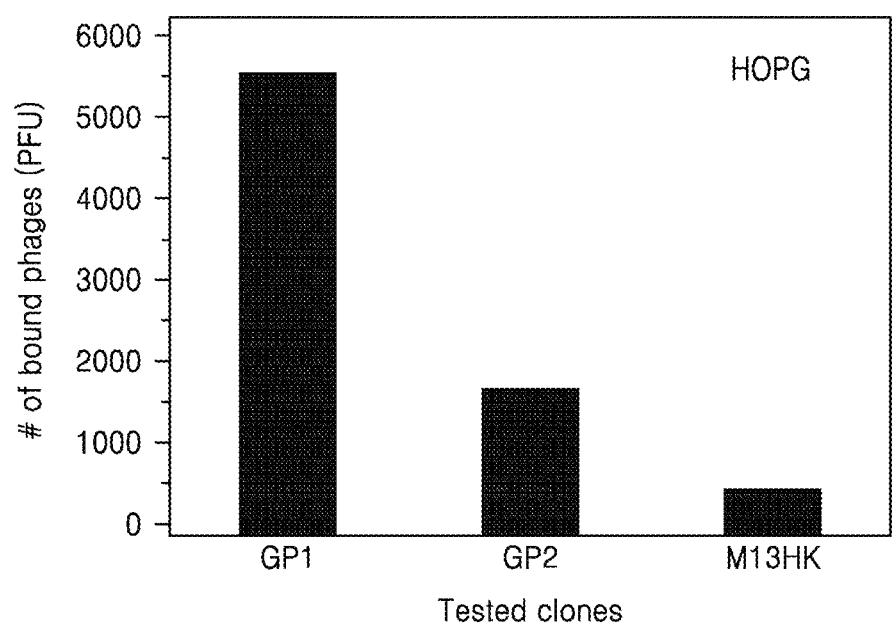
FIG. 3 shows an experimental result of comparing binding affinity of the peptide according to an exemplary embodiment for graphitic surface.

FIG. 3 shows an experimental result of comparing binding affinity of the peptide according to an exemplary embodiment for graphitic surface.

As shown in FIG. 3, the peptide according to a specific embodiment, GP1 (SEQ ID NO: 7) or GP2 (SEQ ID NO: 8) has binding affinity similar to that of P8 GB#1 or P8 GB#5, respectively.

4. Characterization of Peptide Sequences

Figure 4:
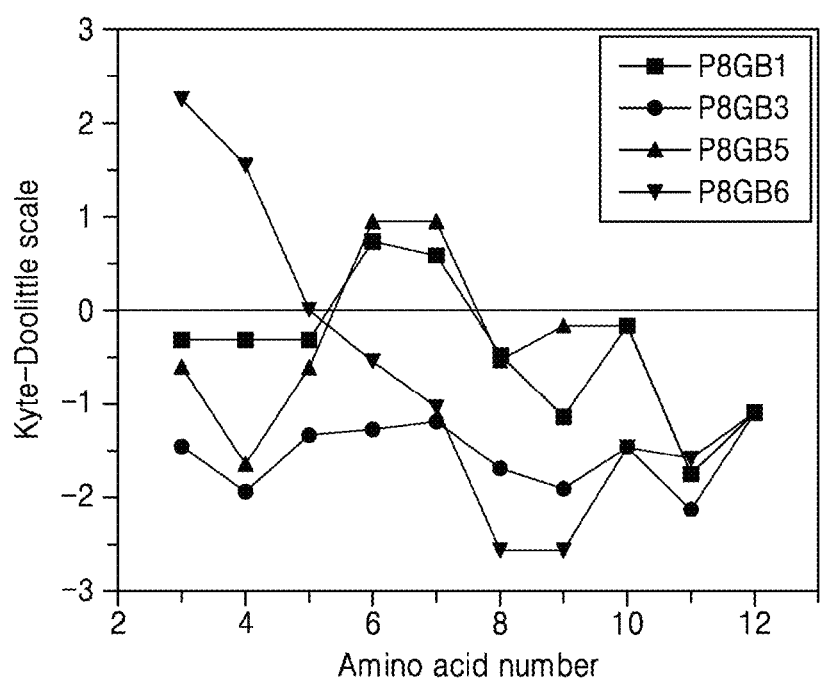
FIG. 4 is a graph showing a relationship between an amino acid sequence of the peptide according to an exemplary embodiment and its hydrophobic property.

As shown in 3 of Example 1, to investigate why P8 GB#1 and #5 have significantly higher binding affinity than p8 GB#3 and #6, the hydrophobic property of each peptide sequence is analyzed according to the Kyte-Doolittle scale (window size=5), and the result is shown in FIG. 4. In FIG. 4, the more positive (+) value in the ordinate means stronger hydrophobicity, and the more negative (−) value means stronger hydrophilicity.

FIG. 4 is a graph showing a relationship between an amino acid sequence of the peptide according to an exemplary embodiment and its hydrophobic property.

As shown in FIG. 4, both the peptide sequences p8 GB#1 and p8 GB#5 according to an exemplary embodiment show high hydrophobicity of 0.6 or higher in the $5^{th}$ to $6^{th}$ amino acid sequences. The reason why p8 GB#1 exhibits higher binding affinity than p8 GB#5 may be due to the presence of the aromatic tryptophan (W) residue in p8 GB#1. That is, it is thought that the presence of the aromatic residue having good reactivity with the graphitic surface in the middle of the amino acid sequence of p8 GB#1 leads to high binding affinity. In contrast, it is thought that P8 GB#3 and P8 GB#6 exhibit low binding affinity for the graphitic surface because they show low hydrophobicity in the $5^{th}$ to $6^{th}$ amino acid sequences. Although p8 GB#3 also has the aromatic tryptophan residue, p8 GB#3 has low hydrophobicity in the $5^{th}$ to $6^{th}$ amino acid sequences, and the hydrophobic property has a stronger effect on the binding affinity than the presence of the aromatic residue. In case of p8 GB#6, a portion of the sequence has hydrophobic property but the amino acids in the 5$^{th}$ and 6$^{th}$ positions are hydrophilic. As a result, it exhibits even lower binding affinity than the negative control p8 GB#8 (EGE). This may be because the inserted peptide p8 GB#6 inhibits even the non-specific binding of the phage.

Example 2. Preparation of Graphitic Material Bound with Peptide-Displaying M13 Phage 1. Preparation of Graphene Bound with Peptide-Displaying M13 Phage Graphene, on which the M13 phage displaying the peptide of SEQ ID NO: 1 according to an embodiment of the present disclosure is arranged, is prepared.

First, an M13 phage including the peptide sequence p8 GB#1 (SEQ ID NO: 5) is prepared using the biopanning method used in Example 1. Considering that the distance between phages may increase at higher pH because of increased electrostatic repulsion between the phages, a phage solution having a concentration of $1 \times 10^{13}$ viral particles/ml is prepared using ultrapure distilled water adjusted to pH 7.0. The concentration of the phage solution may be calculated by the following Equation 1.

Phage concentration(viral particles/mL)=$1.6 \times 10^{16} \times$ O.D. viral solution/7237 [Equation 1]

Then, graphene (product name: kish graphite, manufacturer: Covalent) is placed on a SiO$_2$/Si substrate (product name: EPI-Prime Si wafer with 300 nm dry oxidized SiO$_2$, manufacturer: SILTRON INC, Korea) using a taping method. The substrate with the graphene placed thereon is dipped in the prepared solution of the phage on which the p8 GB#1 peptide is displayed, and then pulled up at a rate of 10 μm/min out of the solution (dip coating method). The phages are arranged on the surface of the substrate pulled up due to binding of the peptides, which is observed by atomic force microscopy (AFM). The images are shown in FIGS. 5 and 6.

Figure 5:
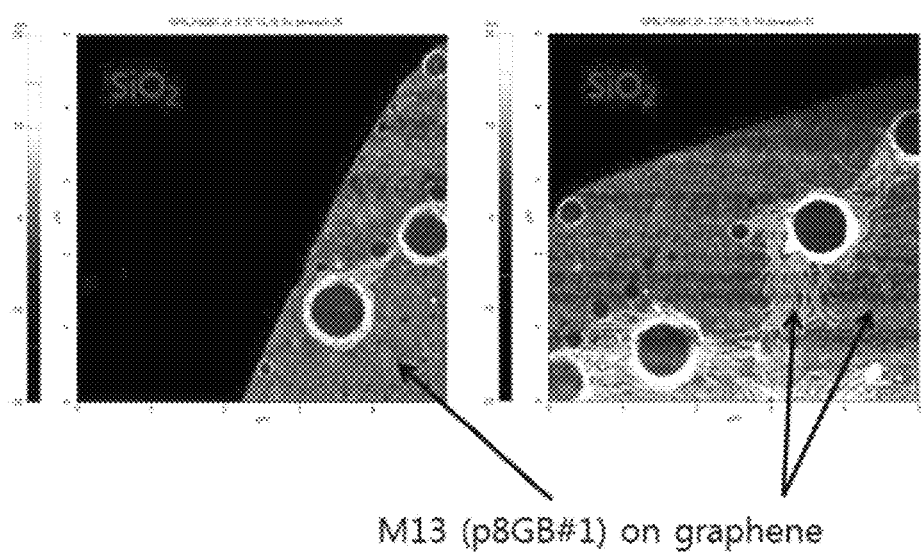
FIG. 5 shows atomic force microscopic images obtained after aligning phages displaying the peptide according to an exemplary embodiment on the surface of graphene.
Figure 6:
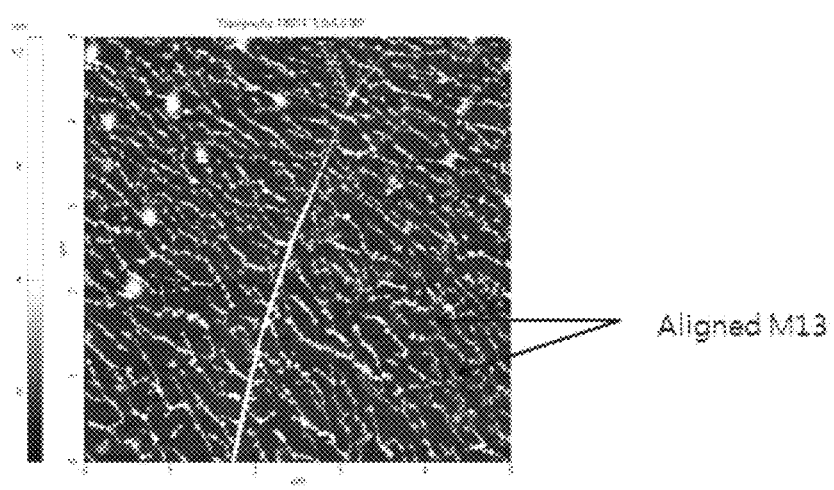
FIG. 6 shows atomic force microscopic images obtained after aligning phages displaying the peptide according to an exemplary embodiment on the surface of graphene.

FIGS. 5 and 6 show atomic force microscopic images obtained after aligning phages displaying the peptide according to an exemplary embodiment on the surface of graphene.

As shown in FIG. 5, when the surface of a nanomaterial is photographed by AFM, the higher portion looks brighter. The SiO$_2$ substrate looks black with low brightness, and the graphene looks brighter. This suggests that the phage including the peptide according to an exemplary embodiment is not bound to the SiO$_2$ substrate but is bound only to the graphene surface. Accordingly, it can be seen that the peptide according to an exemplary embodiment has high selectivity and specificity for the graphene surface.

The large circles on the graphene surface shown in FIG. 5 are air bubbles, which are formed on the graphene surface. It can be confirmed that the phage covers the graphene surface in one layer, except for the air bubbles. Also, it can be seen that, around the air bubbles, the phage immobilized by the air bubble is not directly bound to the graphene but is bound to the phage bound to the graphene, thereby forming a double layer. In particular, referring to the right image of FIG. 5, since the phages around the air bubbles repel one another, contact is minimized and the individual phages are clearly seen. In contrast, the phages bound to the graphene are flattened to maximize the binding area because of the strong binding affinity between the peptide included in the phage and the graphene. That is, the individual phages are not clearly seen but the phages are seen to be arranged on the graphitic surface as one structure, thus forming a functionalized system.

Referring to FIG. 6, it can be seen that the phage is aligned well in a predetermined direction on the graphene in spite of the morphological change of the phage due to the binding to the graphene. Specifically, because the peptide according to an exemplary embodiment is included in the body coat protein, p8, of the M13 phage, the phage is arranged in a thread-like shape owing to strong binding affinity of the peptide for the graphene surface. In particular, it can be seen that the thread-like phages are aligned in a row in the same direction. This result indicates that a material having a graphitic surface may be anisotropically functionalized by arranging the phage on the material having the graphitic surface with directionality.

2. Preparation of Carbon Nanotube Bound with Peptide-Displaying M13 Phage 2.1. Preparation of Colloid Solution First, an aqueous solution is prepared by adding 2% w/v sodium cholate as a surfactant to distilled water and a colloid solution is prepared by stabilizing a single-walled carbon nanotube (manufacturer: Nanointegris, SuperPure SWNT, solution type, 250 mg/mL,) with the sodium cholate by dialysis for 48 hours.

Assuming that an average length and an average diameter of the carbon nanotube (CNT) are 1 μm and 1.4 nm, respectively, the number of the single-walled carbon nanotube included in the colloid solution may be calculated according to the following equation.

Number of single-walled carbon nanotube(/mL)=concentration (μg/mL)$\times 3 \times 10^{11}$ CNT [Equation 2]

The number of the single-walled carbon nanotube included in the colloid solution is calculated as $7.5 \times 10^{13}$/mL by Equation.

2.2. Preparation of Peptide-Displaying Phage

Peptide-displaying phages are prepared by two methods. The peptide-displaying phages are prepared in the same manner as in 2 of Example 1 or by a genetic recombination method.

M13 phage displaying the peptide of SEQ ID NO: 5 on p8 is prepared by the genetic recombination method. Primers of SEQ ID NOs: 17 and 18 are annealed at 95° C. for 2 minutes and cooled to 25° C. at a rate of 0.1° C./s. Then, the M13HK vector is digested with the restriction enzymes BspHI and BamHI (after reaction with the enzymes at 37° C. for 2 hours, the enzymes are inactivated at 65° C. for 20 minutes), and then reacted with T4 DNA ligase (NEB, product# M0202S) at 16° C. for 12 hours to obtain a circular vector. The ligated circular DNA is inserted into electro-competent E. coli (XL-1 Blue cell line, Agilent, product#200228) through electroporation, and genetically recombined M13 phage is amplified by culturing in a shaking incubator at 37° C. for 6 hours (following the instruction of the product manual for product#200228, Agilent). In order to purify the phage from the culture in which the phage and E. coli are mixed, the culture medium is centrifuged at 8000 rpm for 30 minutes and only the supernatant is taken. Since the phage is included in the supernatant, the separated supernatant is mixed with 20% w/v polyethylene glycol (Molecular weight 8000, Promega corporation, product# V3011)/NaCl solution, with a volume of ⅙ of that of the supernatant solution, and centrifuged at 12000 rpm for 30 minutes after reaction at 4° C. for about 16 hours. After discarding the supernatant from the resulting solution, the remaining phage is dissolved in TBS (Dako, product# S3001) to obtain a phage solution. The concentration of the phage solution is calculated according to Equation 1.

The phage solution obtained by the above method may be amplified repeatedly using *E. coli*. The phage is amplified using *E. coli* (XL-1 blue cell line) in early-log state (overnight culture diluted to 1/100). The amplified phage is purified in the same manner as described above.

2.3. Preparation of Carbon Nanotube Bound with Peptide-Displaying M13 Phage

The colloid solution prepared above and a phage solution containing the M13 phage (p8 GB#1) displaying the peptide of SEQ ID NO: 5 are mixed at a molar ratio of 4:1.

Next, for dialysis, each of the mixtures is added to a semipermeable dialysis membrane (SpectrumLab, MWCO 12,000~14,000, product #132 700) tube, and each membrane tube is dialyzed against triple distilled water (resistance >18 Mohm cm) having ion concentration (NaCl) of 0.1 mM. About 16 hours, a thin electronic sheet is formed along the surface of the membrane tube. Next, each membrane tube is transferred to triple distilled water and the electronic sheet is detached by twisting the membrane of the membrane tube and then dried. The electronic sheet thus prepared has a thickness of about 100 nm.

Figure 7:
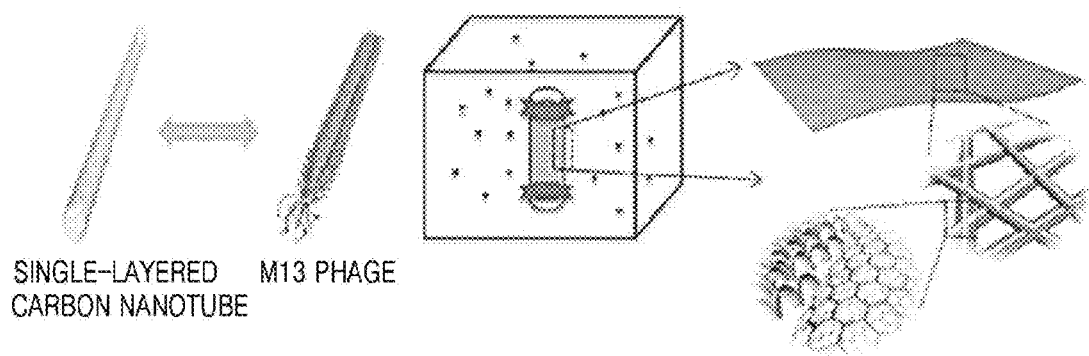
FIG. 7 is a schematic illustration showing a process of preparing carbon nanotube which is bound with M13 phage displaying the peptide according to a specific embodiment.

FIG. 7 is a schematic illustration showing a process of preparing carbon nanotube that is bound with M13 phage displaying the peptide according to a specific embodiment.

As shown in FIG. 7, carbon nanotube is dispersed or dissolved in the colloid material which is stabilized by adding it to the surfactant-containing solution. Single-walled carbon nanotube is bound with about one M13 phage finally to form a sheet having a percolated network structure of carbon nanotube and M13 phage.

Figure 8:
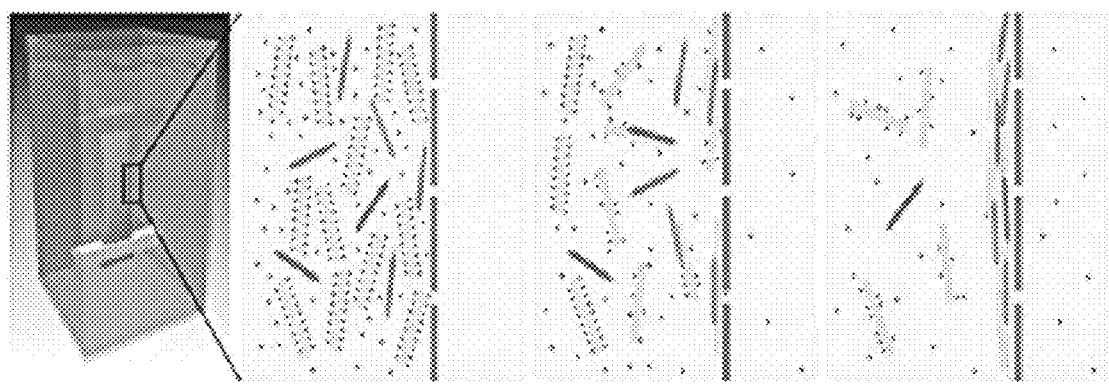
FIG. 8 is a schematic illustration showing a formation principle of the carbon nanotube that is bound with M13 phage displaying the peptide according to a specific embodiment.

FIG. 8 is a schematic illustration showing a formation principle of the carbon nanotube that is bound with M13 phage displaying the peptide according to a specific embodiment.

As shown in FIG. 8, formation of the carbon nanotube bound with M13 phage displaying the peptide according to an exemplary embodiment may be achieved by adding the mixture of the phage solution and the colloid solution to the membrane tube, followed by dialysis against the dialysis solution. While the dialysis proceeds, the concentration of the surfactant, which is attached on the surface of the carbon nanotube in the colloid material and stabilizes the carbonaceous material, in the tube decreases due to diffusion owing to a concentration difference inside and outside the membrane. This diffusion-driven dilution is the most prominent near the membrane. Since the M13 phage displaying the peptide having strong binding affinity to carbon nanotube can begin reacting with the carbon nanotube only when the concentration of the surfactant surrounding the carbon nanotube is low, the binding occurs near the membrane where the dilution occurs the most actively, when the dialysis proceeds for a predetermined time. Based on this principle, a sheet may be formed through dialysis.

Example 3. Test of Binding Affinity to Volatile Organic Compounds

In order to examine whether the peptides selected in Example 1, GP1 (SEQ ID NO: 3) and GP2 (SEQ ID NO: 4) selectively react with volatile organic compounds, binding affinity is tested in liquid phase and gas phase.

1. Test of Binding Affinity to Benzene

Figure 9A:
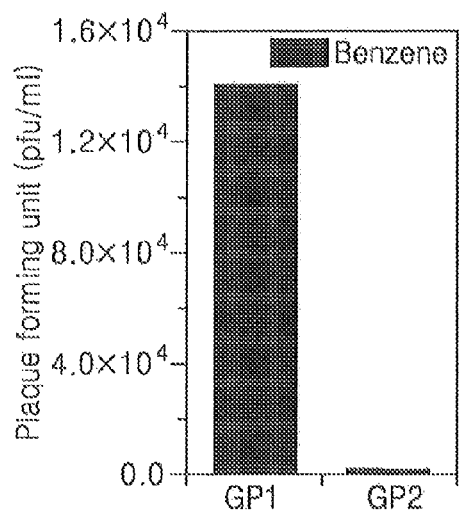
FIGS. 9A through 9C show results of analyzing affinity of the peptide according to an exemplary embodiment for benzene in liquid phase and gas phase.

First, a substrate having a benzene-immobilized HOPG surface is treated with GP1 or GP2-displaying phage, and the number (PFU) of the phage bound with benzene is counted, and the result is shown in FIG. 9A.

Next, a microcantilever system is used for gas phase sensing. The cantilever system consists of four compartments, with each compartment including three cantilevers. Separate compartment enables independent functionalization of the cantilevers. Cantilevers in the fourth compartment are used as references. For peptide immobilization, Cr (10 nm)/Au (50 nm) layers are deposited onto the microcantilevers. The surface is cleaned in piranha solution (4:1 ratio of $H_2SO_4$ (98.08%) and $H_2O_2$ (34.01%)) to remove any contaminants present on the surface, and then rinsed with deionized water. Thiolated peptides (50 μL of 10 μM solution) are immobilized on the gold surface of cantilevers at room temperature for 5 hours. The peptide-conjugated microcantilevers are rinsed with DI/ethanol and dried under nitrogen. For measurements, the peptide-conjugated microcantilevers are enclosed within a chamber containing an inlet and an outlet for the gas flow. Moisture during measurements is monitored with an integrated sensor in the chamber. The flow rate of all gases is controlled at 100 standard cubic centimeter per minute (sccm) using a mass flow controller (MFC). Before the measurement, the microcantilevers are stabilized by nitrogen at 100 sccm overnight. Then, benzene gas is blown for 10 minutes, and changes in resonance frequency (ΔHz) are examined. The results are shown in FIG. 9B.

Figure 9B:
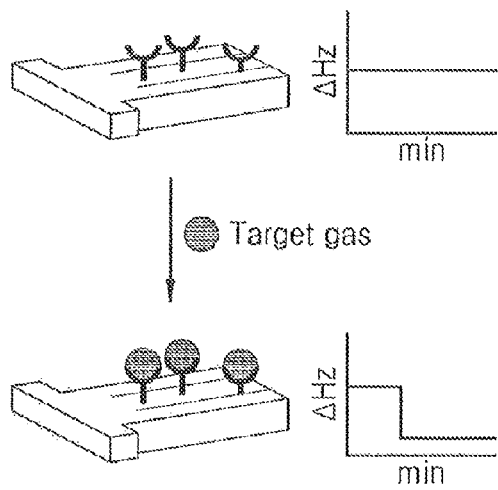
Figure 9C:
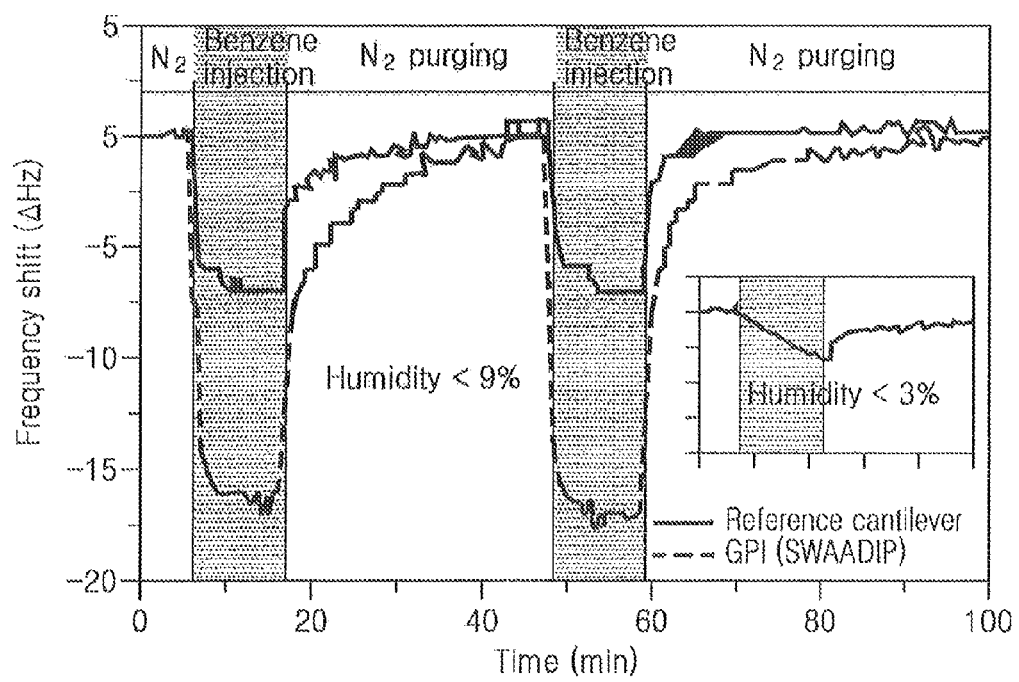

Additionally, benzene gas with moisture of about 9% and about 1 is directly injected to the microcantilever sensor, and the result is shown in FIG. 9C.

FIGS. 9A through 9C show results of analyzing affinity of the peptide according to an exemplary embodiment for benzene in a liquid or gas phase.

As shown in FIG. 9A, in a liquid phase, the GP1 peptide exhibits affinity to benzene, whereas GP2 peptide exhibits a weak reaction with benzene.

As shown in FIG. 9B, when the target molecules bind to the cantilevers, the resonance frequency downshifts. This result indicates that a difference in resonance frequency between peptide-immobilized cantilevers and non-peptide-immobilized reference cantilevers is proportional to concentration of the gas applied, and this principle may be applied to a gas sensor.

As shown in FIG. 9C, when benzene gas with moisture of about 9% is injected to the cantilever sensor, there is a great change in resonance frequency shift. In contrast, at moisture of less than 1%, there is no change in resonance frequency shift. This result indicates that the peptide is active under humid environment, and GP1 peptide has affinity to benzene gas.

2. Test of Reactivity to 6 Kinds of Gases

The peptide sequences selected in Example 1, GP1 and GP2 are immobilized onto the cantilever sensors, respectively in the same manner as in 1 of Example 3, and then 6 kinds of gases of benzene, toluene, xylene, hexane, acetone, and ethanol are applied to the sensor so as to test their reactivity. In this regard, a reaction time is 10 minutes, and a N2 purging time is 25 minutes. Gas injection is conducted in this order of benzene (4032 ppm), toluene (5026 ppm), xylene (6039 ppm), hexane (5299 ppm), acetone (8798 ppm), and ethanol (1473 ppm), and the results are shown in FIGS. 10 and 11.

Figure 10:
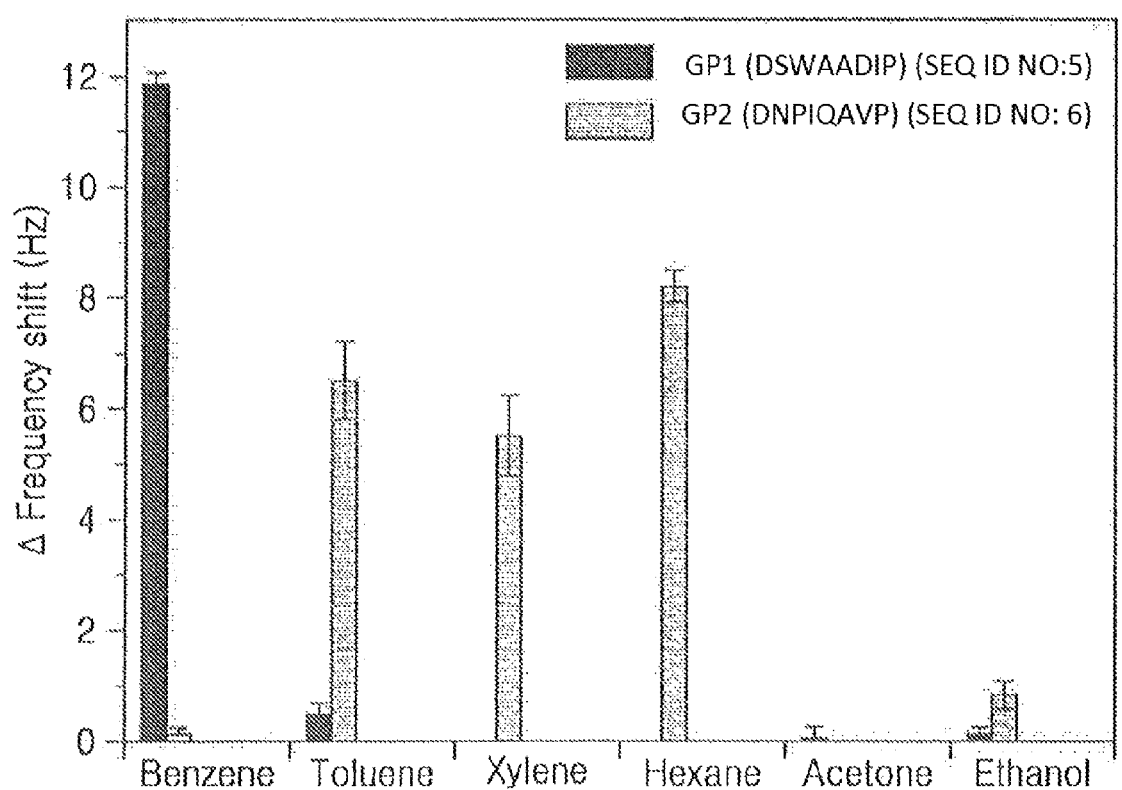
FIG. 10 shows a result of evaluating reactivity of the peptide according to an exemplary embodiment for 6 kinds of gases of benzene, toluene, xylene, hexane, acetone, and ethanol.

FIG. 10 shows a result of evaluating reactivity of the peptide according to an exemplary embodiment for 6 kinds of gases of benzene, toluene, xylene, hexane, acetone, and ethanol.

As shown in FIG. 10, GP1 shows the highest reactivity to benzene, and GP2 shows the highest reactivity to toluene, indicating that GP1 has excellent selectivity for benzene and GP1 has excellent selectivity for toluene among the volatile organic compounds.

Figure 11A:
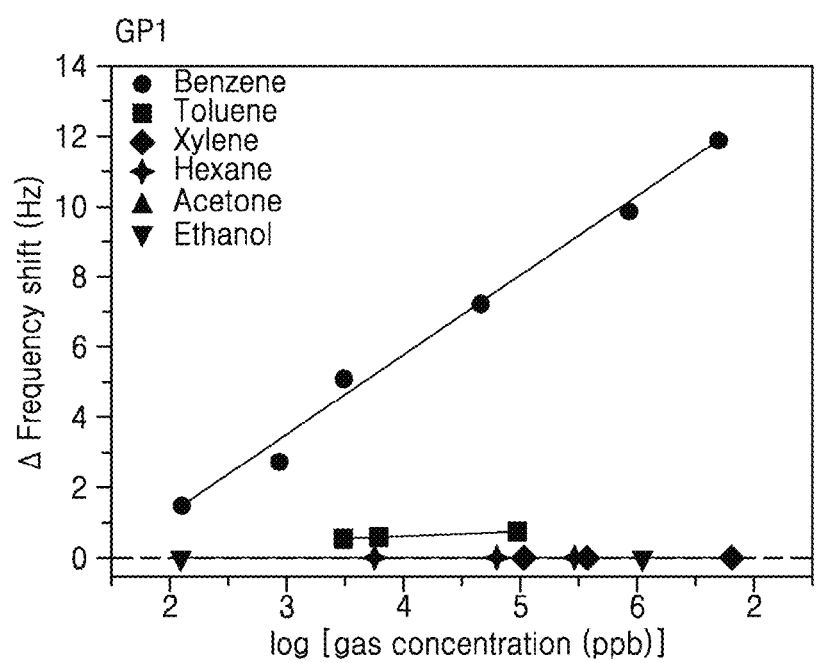
FIGS. 11a through 11b show results of quantitatively analyzing concentrations of the collected gases to evaluate reactivity of the peptide according to an exemplary embodiment for 6 kinds of gases of benzene, toluene, xylene, hexane, acetone, and ethanol (B: benzene, T: toluene, X: xylene, H: hexane, A: acetone, E: ethanol)
Figure 11B:
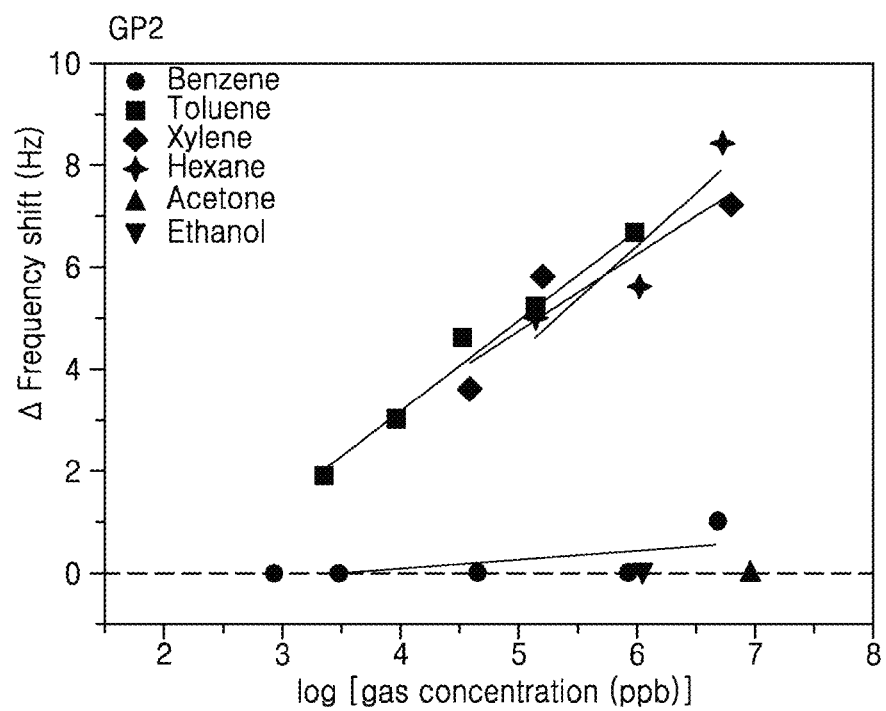

FIGS. 11a through 11b shows results of quantitatively analyzing concentrations of the collected gases to evaluate reactivity of the peptide according to an exemplary embodiment for 6 kinds of gases including benzene, toluene, xylene, hexane, acetone, and ethanol (B: benzene, T: toluene, X: xylene, H: hexane, A: acetone, E: ethanol).

As shown in FIG. 11a, GP1 has excellent selectivity for benzene, which is consistent with the result of FIG. 10. As shown in FIG. 11, GP2 has excellent selectivity for toluene gas.

What is claimed is:

1. A peptide or peptide set comprising
one or more amino acid sequences selected from the group consisting of SEQ ID NOs: 5 to 8, wherein the peptide or peptide set is no more than 60 amino acids in length.

2. The peptide or peptide set of claim 1, wherein the peptide or peptide set specifically binds to a graphitic material, and wherein the graphitic material is selected from the group consisting of graphite, graphene, highly ordered pyrolytic graphite (HOPG), carbon nanotube, and fullerene.

3. The peptide or peptide set of claim 1, wherein the peptide or peptide set is displayed on a coat protein of a phage or a fragment thereof, and wherein the C-terminus of the peptide or peptide set is linked to the N-terminus of a coat protein of the phage, or the peptide or peptide set is inserted between consecutive amino acid sequences of the coat protein of the phage or replaces the consecutive amino acid sequences of the coat protein.

4. The peptide or peptide set of claim 3, wherein the peptide or peptide set comprising the amino acid sequences of SEQ ID NOs: 5 or 7 specifically binds to benzene, and the peptide or peptide set comprising the amino acid sequences of SEQ ID NOs: 6 or 8 specifically binds to toluene, xylene, hexane or a combination thereof.

5. The peptide or peptide set of claim 4 for use in detecting or eliminating a volatile organic compound selected from the group consisting of benzene, toluene, xylene, and hexane,
wherein the peptide or peptide set specifically binding to benzene comprises the amino acid sequences of SEQ ID NOs: 5 or 7, and the peptide or peptide set specifically binding to toluene, xylene, or hexane comprises the amino acid sequences of SEQ ID NOs: 6 or 8.

6. The peptide or peptide set of claim 1, wherein the peptide or peptide set specifically binds to highly ordered pyrolytic graphite (HOPG).

7. The peptide or peptide set of claim 1, wherein the peptide or peptide set comprising SEQ ID NOs: 5 or 7 specifically binds to graphene or carbon nanotube.

8. A peptide or peptide set consisting of one or more amino acid sequences selected from the group consisting of SEQ ID NOs: 5 to 8.

9. A phage, comprising the peptide or peptide set of claim 1 displayed on a coat protein of the phage or a fragment thereof.

10. The phage of claim 9, wherein the phage is M13 phage, F1 phage, Fd phage, If1 phage, Ike phage, Zj/Z phage, Ff phage, Xf phage, Pf1 phage, or Pf3 phage.

11. The phage of claim 9, wherein the C-terminus of the peptide or peptide set is linked to the N-terminus of a coat protein of the phage, or the peptide or peptide set is inserted between consecutive amino acid sequences of the coat protein of the phage or replaces the consecutive amino acid sequences of the coat protein.

12. The phage of claim 11, wherein the coat protein is selected from the group consisting of p3, p6, p8 and p9 of M13 phage.

* * * * *